United States Patent [19]

Bhattacharya et al.

[11] Patent Number: 4,582,993
[45] Date of Patent: Apr. 15, 1986

[54] VOID DETECTION IN CAST METAL

[75] Inventors: Sabyasachi Bhattacharya; Graham B. Wills, both of London, England

[73] Assignee: Prescot Rod Rollers Limited of C.C.R. Plant, Merseyside, England

[21] Appl. No.: 619,915

[22] Filed: Jun. 12, 1984

[30] Foreign Application Priority Data

Jun. 20, 1983 [GB] United Kingdom ................ 8316746

[51] Int. Cl.⁴ .......................................... G01N 23/18
[52] U.S. Cl. ................................. 250/359.1; 378/58
[58] Field of Search ............... 250/358.1, 359.1, 360.1; 378/58

[56] References Cited

U.S. PATENT DOCUMENTS 4,393,313  7/1983  Calkins et al. ...................... 250/560
4,415,980  11/1983  Buchanan ............................. 378/58
4,549,306  10/1985  Shideler et al. ...................... 378/58

FOREIGN PATENT DOCUMENTS 55971  7/1982  European Pat. Off.
404004  10/1973  U.S.S.R. ............................... 378/58

OTHER PUBLICATIONS

R. C. Woods and L. P. Kenna, "A New Use for X-Rays in Industry" *Electronics* (Apr. 1941), pp. 29-31, 89-91.
L. W. Mysovski and G. S. Ismailova, "The Illumination of Metallic Castings by Gamma Rays, With the Object of Detecting Cavities and Other Defects" *Reports of the Academy of Sciences of U.S.S.R.* [A], (2), (1926), pp. 29-31.
P. Elsip & R. J. Lewis, "Television and Industrial Fluoroscopy", Reprinted from *The British Journal of Non-Destructive Testing*, vol. 6-No. 1, (1964).
Andrex NDT Systems, *X-Ray Imaging Detectors*, sales brochure.
Marconi Instruments Limited, sales brochure.

*Primary Examiner*—Alfred E. Smith
*Assistant Examiner*—Constantine Wannaher
*Attorney, Agent, or Firm*—Parkhurst & Oliff

[57] ABSTRACT

A method of, and apparatus for, detecting voids in or on the surface of cast metal comprises passing a substantially collimated beam of photons through the cast metal, detecting the photon flux emerging from the cast metal with a photon detector, and estimating the size and location of any void present in or on the cast metal from the standard deviation of the output of the photon detector with calculating means.

15 Claims, 3 Drawing Figures

VOID DETECTION IN CAST METAL

This invention relates to a method of detecting voids in or on the surface of cast metal. The invention has especial, though not exclusive, use with a continuous casting process in which molten metal is cast in a machine comprising a casting wheel having a peripheral groove and, closing an arcuate length of the groove to form a mould, a continuously moving endless band, to obtain cast bar from which metal rod or wire can be formed.

Voids can be formed in the metal or on the metal surface during the casting process. These voids may be oxidised due to the presence of air. Although subsequent rolling of the bar to rod usually removes the void, the oxide remains producing central defects. Subsequent drawing of the rolled rod to wire will usually result in breakage due to the presence of the defects. By detecting the presence and size of voids in the cast metal bar, the information obtained can be used to optimise the casting process and/or to grade the quality of the cast (and rolled) metal.

The problem with this method is that the voids have to be detected within or on the continuously cast bar whilst the bar is moving and at a high temperature (but below its melting point). A known technique uses ultrasonic measurement. This has the disadvantage that direct physical contact has to be made with the cast bar which is at a high temperature (for example, in the case of copper the cast bar can be in excess of 700° C.).

An alternative technique is continuous fluoroscopy which requires a high intensity radiation source. This can be provided by an X-ray set, but X-ray tubes have limited lives and are not well suited for monitoring continuous processes. As an alternative a high activity radioactive source of suitable half-life may be used. In both cases massive radiation shielding is required to make the equipment safe for on line application. The fluorescent image has to be viewed by a closed circuit television system, usually incorporating an image intensifier. The interpretation of the televised image must be done visually or by analysis of the video signals.

It is an object of this invention to provide a method of detecting voids in or on the surface of cast metal which overcomes the above mentioned disadvantages.

According to the present invention a method of detecting voids in or on the surface of cast metal comprises passing a substantially collimated beam of photons from a photon source through the cast metal, detecting the photon flux emerging from the cast metal with a photon detector, and estimating the size of any void present in or on the cast metal from the output of the photon detector with calculating means.

The output from the photon detector is a function of the photon flux incident upon it, and the photon flux is a function of the total metal in the beam path. The presence of a void, representing a loss of metal in the beam path, produces an increase in the photon flux received by the photon detector and a subsequent increase in the output signal.

The photon source is preferably a radioactive source (for example, cesium-137) producing gamma rays. Alternatively the source may be a low intensity X-ray generator, preferably operating from a DC potential.

Preferably the photon detector is an ionisation chamber, a photomultiplier/crystal detector or a geiger counter.

Preferably a non-contacting width measuring device is connected to the calculating means. The width measurer monitors the width of the cast metal in the direction of the photon path and detects any variation therein. Such information is fed to the calculating means which allows for any such variations. The width measurer is preferably an optical device.

The calculating means is preferably a programmable controller (for example, a microprocessor or microcomputer) which digitally processes the output signal from the photon detector. This can maximise the signal to noise ratio of the system and thereby give the maximum detection sensitivity proportional to a given application.

The basis on which the calculating means operates is as follows:

Let $N_x$ = counting rate in counts/sec. when solid cast metal bar is present in the beam path.

$n_x$ = counting rate in counts/sec. when a void of given dimensions is present in the beam path.

$t_x$ = period for which the count rate is measured.

$$\Delta_x = t_x(n_x - N_x)$$

$\sigma_x$ = standard deviation in $\Delta_x$ $$= \pm \sqrt{t_x(n_x + N_x)} \text{ counts}$$

The calculating means is then programmed to measure successive values of $\Delta_x$, in successive integrating periods $t_x$, to calculate in each case $\sigma_x$ or a sufficient approximation thereof, to calculate the value of the difference, $$(\Delta_x - |p\sigma_x|)$$

(where p is a number set to allow for spurious signals) and, if this is positive, to sound an alarm and to record and/or display the magnitude of this difference.

The probability that a result $$(\Delta_x - |p\sigma_x|) > 0$$

indicates a void rather than random fluctuations in the radiation flux emitted from the radiation source depends on the value set for p and the size of the void. Preferably the value of p is at least 2 and the calculating means is programmed so that values of p greater than 2 may be selected as desired.

The sensitivity of the system for detecting a void can be described approximately by the condition:

$$\Delta_x/\sigma_x = t_x N_x(K-1)/\sqrt{[t_x(K+1)N_x]} \geq p$$

$$= [\sqrt{(t_x N_x)}][(K-1)/\sqrt{(K+1)}] \geq p$$

where:
$t_x$ = integrating time = L/V s.
L = dimension of void measured in direction of motion of bar, mm
V = velocity of bar, mm/s
K = $n_x/N_x$ For essentially cylindrical voids having their axes coincident with the axis of the bar we have found, for a copper bar and a source of cesium-137, that:

$$K \approx k \exp(qd)$$

where:
- d = diameter of void, mm
- q = constant depending on system geometry and absorption coefficient of the bar material for the radiation used = 0.018 mm$^{-1}$
- k = constant related to system geometry = 0.87

In any practical system the bar material, the radiation geometry and the radiation energy are fixed consequently K will vary essentially exponentially with the void diameter d, decreasing as the diameter decreases.

The smallest diameter of void that can be detected whilst satisfying the condition that $\Delta_x/\sigma_x \geq p$ will therefore be determined by the count rate $N_x$ measured on solid bar and on the integrating time $t_x$.

The magnitude of $N_x$ will be set by the practical limits of the counting system and the source of radiation flux. The only variable which can be adjusted to increase the system sensitivity is the integrating time $t_x$. It can be shown that the optimum value for $t_x = L/V$. It is essential therefore if the maximum sensitivity of the system is to be realised to be able to adjust $t_x$ to match the length of the voids passing through the system. Since the lengths of voids will be variable, and cannot be anticipated, the calculating system is programmed to calculate the value of the difference.

$$(\Delta_x - |p\sigma_x|)$$

for successive integrating periods of $t_x$, $2t_x$, $3t_x$, etc. as may be desired, and to signal, record and display the data as previously described. The value of $t_x$ is set equal to the value of L/V for the void of minimum length which it is anticipated will occur in the bar.

If a void is detected or suspected the record or display can be programmed to show
(i) The measuring period $t_x$, $2t_x$, etc. required to produce the signal and consequently this will give an approximate indication of void length L.
(ii) The difference $(\Delta_x - |p\sigma_x|)$ and the value of p chosen which will indicate the degree of confidence which can be placed on the signal and will also give an approximate indication of the diameter of the void.

The calculating means may also be programmed to actuate an audible or visual alarm when a void is detected; to predict when defective cast metal bar will emerge from the rolling mill (where present); to store data on voids and be able to analyse it at a later date; and to communicate with a host computer (for example, a plant computer storing information on stock level, etc.).

This invention also includes apparatus for detecting voids in cast metal as herein described.

This invention has the advantages that voids in or on the surface of cast metal can be detected under dynamic conditions; that long, small diameter voids, and short, large diameter voids can be detected, and that differences between void sizes can be detected and, if required, classified.

This invention is further illustrated, by way of example with reference to the accompanying drawings, in which.

Figure 1:
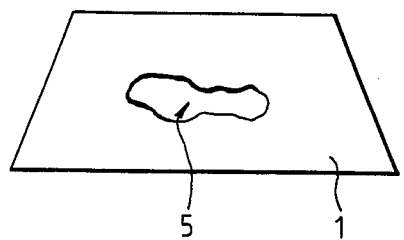
FIG. 1 is a cross-sectional view of a continuously cast copper bar having a void.
Figure 2:
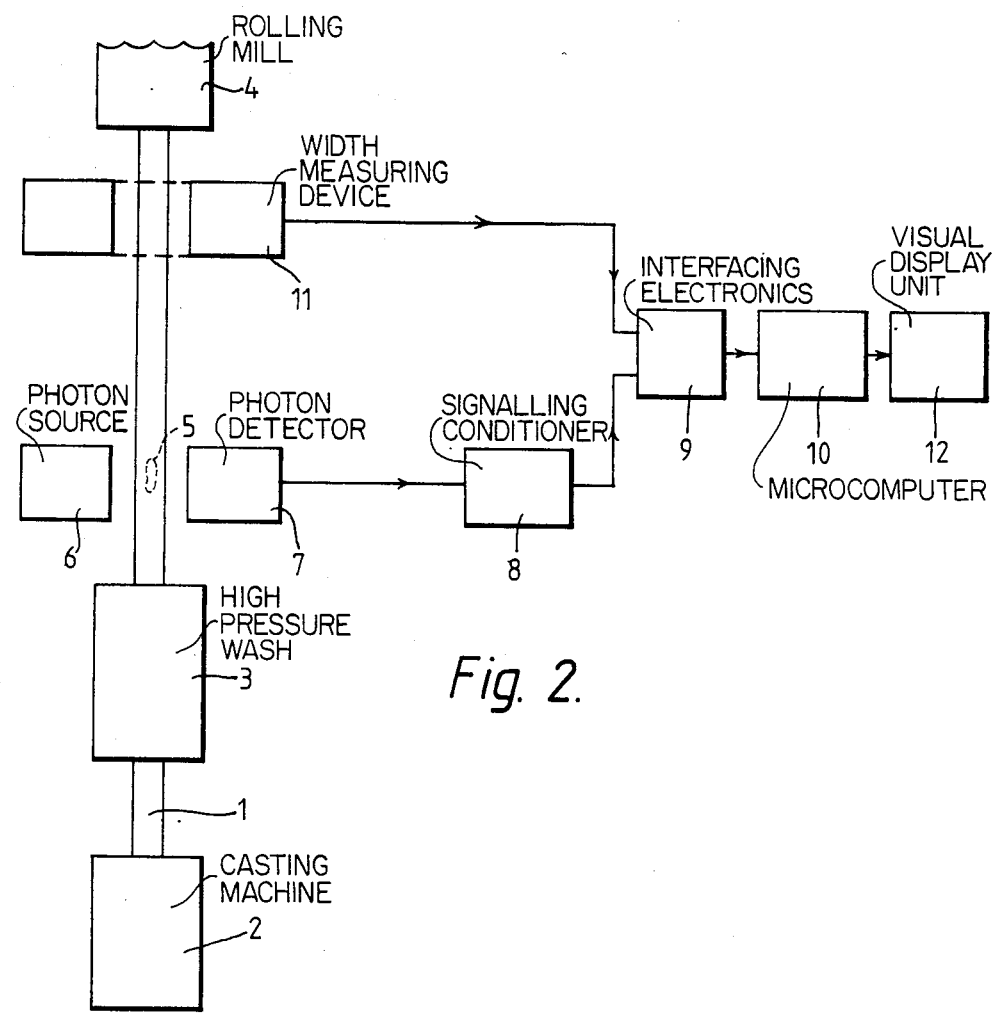
FIG. 2 is a schematic view of a system for detecting voids in the continuously cast copper bar.

Referring to FIGS. 1 and 2, a copper bar 1 is continuously cast from casting machine 2. The cast copper bar 1 then passes through a high pressure wash 3 before entering the rolling mill 4. In order to detect any voids 5 present in the bar 1, a void detection system is positioned between the wash 3 and rolling mill 4. The void detection system comprises a photon source 6 in the form of cesium-137; a photon detector 7 (for example, an ionisation chamber); and calculating means in the form of a microcomputer 10. The output from the photon detector 7, which is a function of the total metal in the beam of photons between the source 6 and detector 7, is passed through a signalling conditioner 8 and interface electronics 9 before entering the microcomputer 10. The microcomputer 10 is programmed to estimate the size of any void 5 present in the copper bar 1 from the output of the detector 7. A non-contacting optical width measuring device 11 is also connected to the microcomputer 10 via the interface electronics 9. From the output from the width measuring device 11, the microcomputer 10 can allow for any variations in the width of the copper bar 1. A visual display unit 12 displays the output from the microcomputer 10.

Figure 3:
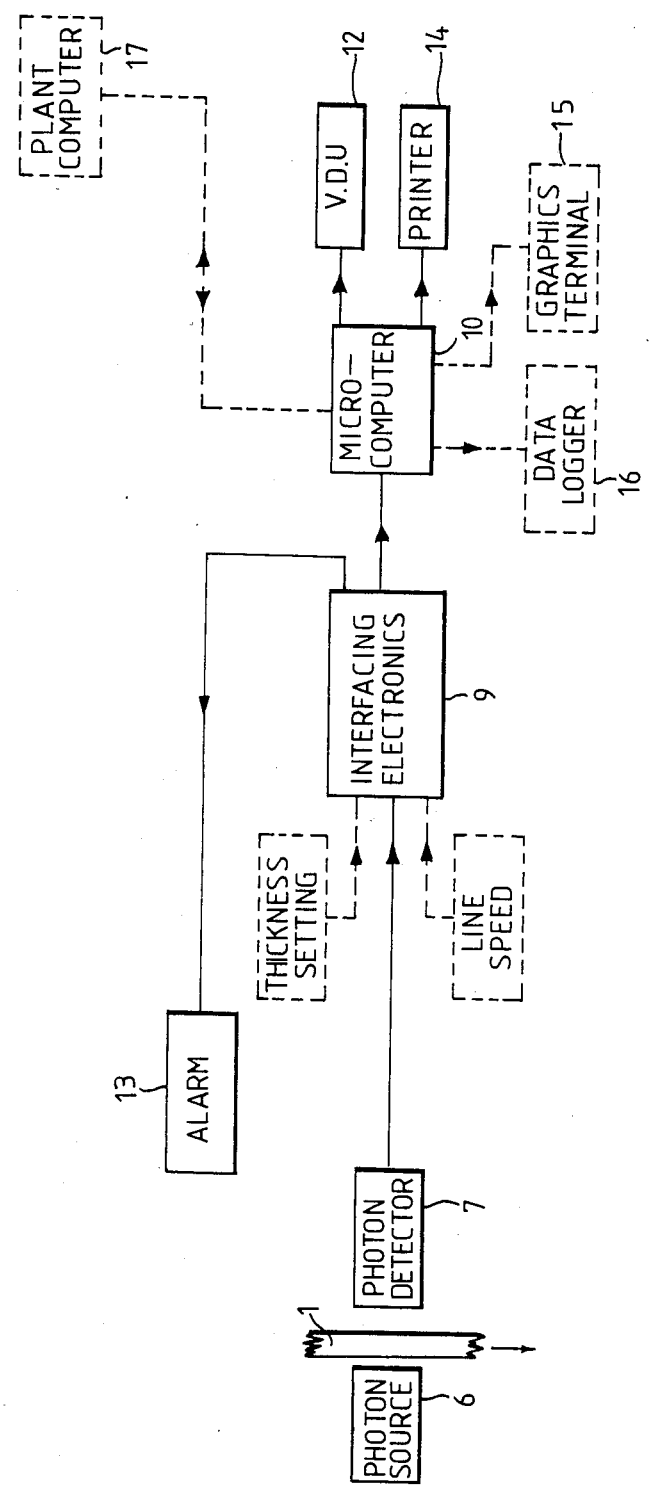
FIG. 3 is a schematic view of an alternative system for detecting voids.

In the alternative arrangement shown in FIG. 3, the thickness of the copper bar 1 is programmed into the microcomputer 10, as is the line speed of the bar 1. These figures are also used to estimate the size and location of any void that is present. The microcomputer 10 is also connected to an alarm 13; a printer 14 for a printed output; a graphics terminal 15 for graphically displaying the output; a data logger 16 for storing data on the voids; and a plant computer 17 which stores information on plant stock levels, etc.

We claim:
1. A method of detecting voids in or on the surface of a moving cast metal element comprising:
   passing a substantially collimated beam of photons from a photon source through the moving cast metal element;
   detecting the photon flux emerging from the moving cast metal element over a predetermined calculating period with a photon detector;
   calculating a factor indicative of the standard deviation of the detected flux for the calculating period; and
   estimating the size of any void present in or on the surface of the cast metal element from the standard deviation factor with calculating means.

2. A method as claimed in claim 1, wherein said photon detector generates an output signal representative of the photon flux and the calculating means comprises a programmable computer which digitally processes the output signal from the photon detector.

3. A method as claimed in claim 2, wherein the programmable computer is programmed to actuate an alarm when a void is detected.

4. A method as claimed in claim 2, wherein the programmable computer is programmed to store data concerning the voids.

5. Apparatus for detecting voids in or on the surface of a moving cast metal element comprising:
   a photon source for producing a substantially collimated beam of photons;
   a photon detector positioned on the opposite side of the moving cast metal element from the photon source and generating an output signal representative of an amount of flux of said photons through said moving cast metal element; and calculating means receiving the output signal from the photon detector and calculating the photon flux emerging from the moving cast metal element over a predetermined calculating period, deriving a factor indicative of the standard deviation of the detected flux over the calculating period, and estimating the size of any void present in or on the moving cast metal element from the standard deviation factor.

6. Apparatus as claimed in claim 5, wherein the photon source comprises a radioactive source emitting gamma rays.

7. Apparatus as claimed in claim 5 wherein the photon detector comprises one of an ionisation chamber, a photomultiplier/crystal detector and a geiger counter.

8. Apparatus as claimed in claim 5, further comprising a non-contacting width measuring device for monitoring the width of the moving cast metal element and transmitting a signal representative thereof to the calculating means.

9. Apparatus as claimed in claim 5, wherein the calculating means comprises a programmable computer.

10. Apparatus as claimed in claim 5, further comprising an alarm, said calculating means being connected to, and able to actuate, said alarm.

11. Apparatus as claimed in claim 5, further comprising visual display means, said calculating means being connected to said visual display means for displaying an output from the calculating means.

12. An apparatus for detecting voids in or on the surface of a moving cast metal component, comprising:

a photon source disposed on one side of the moving cast metal component for producing a substantially collimated beam of photons and directing said beam towards said moving cast metal component;

a photon detector disposed on an opposite side of said moving cast metal component from the photon source for receiving photons of said beam which have passed through said moving cast metal component and generating a signal representative of the amount of flux of said photons from said beam;

calculating means for:

receiving said photon detector signal;

calculating a standard deviation of the detected flux represented by said signal over at least one predetermined basic integration period; and calculating from said standard deviation the size of any void present in or on the surface of the moving cast metal element and generating an output signal representative thereof; and display means for receiving and displaying said output signal from said calculating means.

13. The apparatus as claimed in claim 12, wherein said calculating means further comprises means for:

calculating the standard deviation of said detected photon flux over a plurality of integration time periods; and calculating the size of any void present in the moving cast metal component from each such calculated standard deviation for each such integrated time period and generating an output signal representative thereof for display on said display means.

14. The apparatus according to claim 13, wherein said plurality of integration time periods comprises integral multiples of said pre-determined basic integration period.

15. The apparatus of claim 14, wherein said predetermined basic integration period is selected to be substantially equal to the minimum anticipated value of L/V, where L represents the minimum anticipated length in the direction of motion of voids expected to occur in the moving cast metal component to be measured, and V represents the speed of the moving cast metal component in said direction of motion.

* * * * *